(12) United States Patent
Kennedy

(10) Patent No.: US 8,128,647 B2
(45) Date of Patent: Mar. 6, 2012

(54) SURGICAL INSTRUMENT FOR DETECTING, ISOLATING AND EXCISING TUMORS

(76) Inventor: John S. Kennedy, Stone Mountain, GA (US)

( * ) Notice: Subject to any disclaimer, the term of this patent is extended or adjusted under 35 U.S.C. 154(b) by 424 days.

(21) Appl. No.: 12/339,409

(22) Filed: Dec. 19, 2008

(65) Prior Publication Data

US 2009/0182366 A1 Jul. 16, 2009

Related U.S. Application Data

(63) Continuation-in-part of application No. 11/939,587, filed on Nov. 14, 2007, now abandoned.

(51) Int. Cl.
*A61B 17/32* (2006.01)

(52) U.S. Cl. ........................................... 606/170

(58) Field of Classification Search .......... 606/167, 606/170, 171, 180, 184, 185; 600/562, 564, 600/566, 567

See application file for complete search history.

(56) References Cited

U.S. PATENT DOCUMENTS

| | | | |
|---|---|---|---|
| 847,133 A | 3/1907 | Velasco | |
| 2,379,140 A | 6/1945 | Frank | |
| 2,681,625 A | 6/1954 | Babbitt | |
| 3,512,519 A | 5/1970 | Hall | |
| 4,616,656 A * | 10/1986 | Nicholson et al. | 600/300 |
| 4,785,826 A * | 11/1988 | Ward | 600/567 |
| 5,111,828 A | 5/1992 | Kornberg et al. | |
| 5,183,053 A | 2/1993 | Yeh et al. | |
| 5,267,572 A * | 12/1993 | Bucalo | 600/567 |
| 5,346,497 A | 9/1994 | Simon et al. | |
| 5,353,804 A | 10/1994 | Kornberg et al. | |
| 5,488,958 A | 2/1996 | Topel et al. | |
| 5,499,989 A | 3/1996 | LaBash | |
| 5,613,972 A | 3/1997 | Lee et al. | |
| 5,795,308 A | 8/1998 | Russin | |
| 5,810,806 A * | 9/1998 | Ritchart et al. | 606/45 |
| 5,827,199 A | 10/1998 | Alexander | |
| 5,848,978 A | 12/1998 | Cecchi | |
| 5,919,196 A | 7/1999 | Bobic et al. | |
| 6,080,113 A | 6/2000 | Heneveld et al. | |
| 6,080,114 A | 6/2000 | Russin | |
| 6,331,166 B1 | 12/2001 | Burbank et al. | |
| 6,383,145 B1 * | 5/2002 | Worm et al. | 600/564 |
| 6,551,253 B2 | 4/2003 | Worm et al. | |
| 6,699,206 B2 | 3/2004 | Burbank et al. | |
| D546,452 S | 7/2007 | Gayheart et al. | |
| 2002/0157676 A1 | 10/2002 | Schmieding | |
| 2005/0113716 A1 | 5/2005 | Mueller, Jr. et al. | |
| 2007/0208255 A1 * | 9/2007 | Ridley et al. | 600/459 |
| 2008/0294113 A1 * | 11/2008 | Brockmeier et al. | 604/167.06 |

* cited by examiner

*Primary Examiner* — Kathleen Sonnett
*Assistant Examiner* — Katherine M Shi
(74) *Attorney, Agent, or Firm* — Thomas, Kayden, Horstemeyer & Risley, LLP

(57) ABSTRACT

A cutter (8) is telescopically received in a cannula (9) and both the cutter and cannula are telescopically mounted on a tubular carrier (7). A detection device (6) may be inserted through the open-ended carrier, cutter and cannula to properly place the surgical instrument in alignment with the tumor to be excised. Positioning tines (80) may penetrate the patient to firmly locate the carrier in its proper position on the patient. The cutter and cannula are moved about the carrier and are pressed into the tissue of the patient with the expectation that the circular core (60) of breast tissue formed by the cutter will have clear margins about the tumor. If the tumor extends too close to the circular incision, the cannula may be rotated so that its sidewall opening (26) faces the side of the remaining tissue to be excised and the surgeon can pull the remaining tissue through the sidewall and excise it, thereby avoiding a separate and delayed surgical procedure.

28 Claims, 7 Drawing Sheets

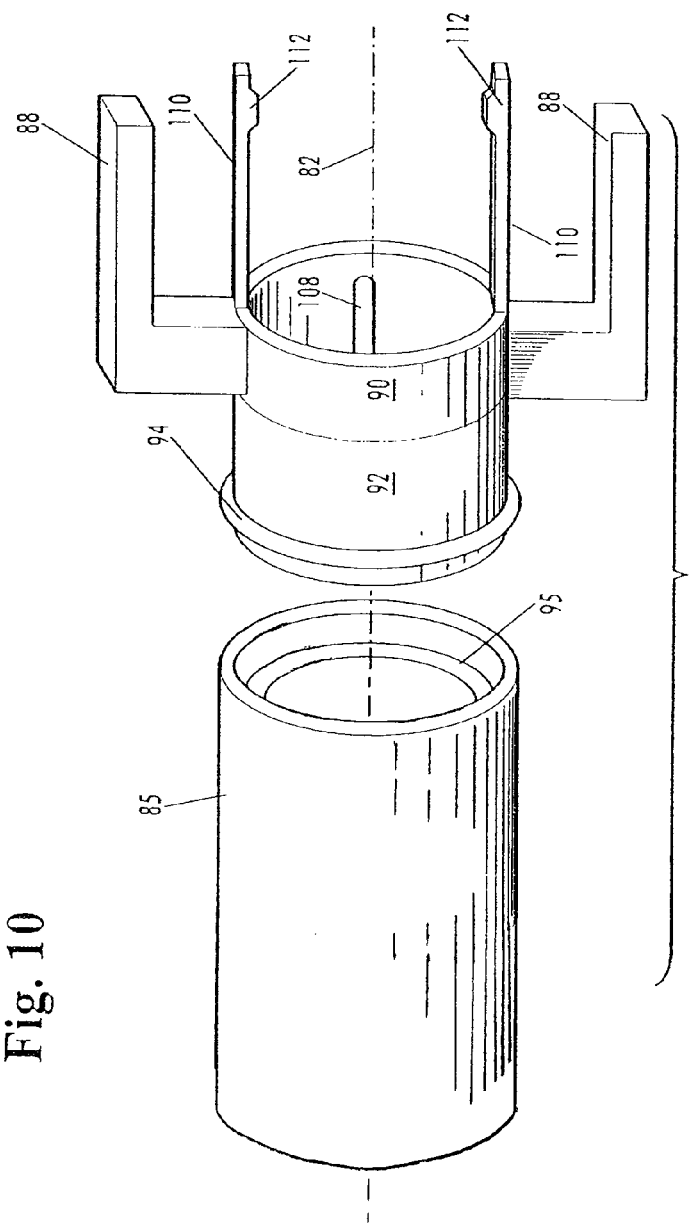
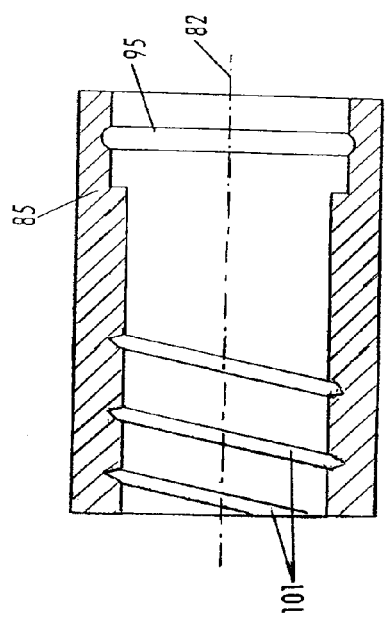
Fig. 9
Fig. 10

SURGICAL INSTRUMENT FOR DETECTING, ISOLATING AND EXCISING TUMORS

CROSS REFERENCE

This is a continuation-in-part of U.S. Utility patent application Ser. No. 11/939,587 filed Nov. 14, 2007 now abandoned.

FIELD OF THE INVENTION

This invention concerns a cutting surgical instrument used by a surgeon during the process of detecting, isolating and excising malignant or non-malignant tumors or other lesions from various parts of the body, particularly for use in lumpectomy, extracting cancerous tumors from the breast.

BACKGROUND OF THE INVENTION

When conducting breast surgery for the removal of tumors, the usual procedure is to locate the position and depth of the tumor by use of palpation, ultrasound, mammogram, or other detection devices. With this information, the surgeon typically makes a shallow incision in the skin so as to pull away the skin from the underlying tissue and then proceeds with surgery through the opening in the skin and into the fat and breast tissue to reach the tumor and excise it.

In recent years, various surgical aids have been developed for reaching and excising tumors. For example, a garrote wire has been used that has a loop that can be inserted over and beneath the tumor. The garrote loop is heated to a temperature sufficient for searing the tissue and the loop is drawn tightly beneath the tumor so as to release the tumor from the rest of the breast. This enables the surgeon to lift the tissue that contains the tumor from the patient. Other improvements include the use of cylindrically shaped cutters that cut a core of tissue from the breast, with the core surrounding the tumor and then excising the core with the tumor contained in the core.

Breast conserving surgery is considered the most desirable surgical option for the majority of women with breast cancer and has become the standard of care for most women with breast cancer. Desirably, the incision should be made about the tumor with a clear negative margin of tissue about the tumor so as to make sure that the entire tumor is excised.

Typically, when the tissue has been removed from the body, a pathologist examines the tissue to determine the nature of the cancerous growth and particularly to determine if the tumor extends beyond the tissue removed from the patient, or if the clear negative margin of tissue about the tumor is not adequate. If a portion of the tumor has been left in the patient or if a clear margin about the tumor is not adequate, a reexcision must be made.

One option for achieving a clear margin would be to remove a much larger amount of tissue about the tumor, however this compromises the cosmetic outcome of a procedure which is intended to conserve the contour of the breast. In addition, excision of more tissue is likely to extend the time for healing and recovery. The risk of bleeding and infection is likely increased as well. Another option for achieving a clear margin is to simply wait for the final pathology report, typically available a few days later. If the tumor has not been completely removed, or if the margin of tissue about the tumor is not adequate, a reexcision can be done. A reexcision would usually be made about two weeks after the initial surgery. The reexcision rates in the published literature range between 15% up to more than 50% of the initial operations. Reexcision usually is demoralizing and a physical ordeal for the patient, let alone the costs, added recovery time, and added risks of a second procedure.

Accordingly, it would be desirable for both the patient and the surgeon to use a device and a process for more reliably detecting the tumor, isolating the tumor and then excising the tumor from the body, with the device and with the procedure forming a small opening in the breast tissue for excising the tumor with a comparatively small amount of surrounding normal breast tissue, and providing the ability to reexcise about the initial excision cavity to form clear negative margins of tissue about the side of the tumor before termination of the overall initial procedure.

SUMMARY OF THE DISCLOSURE

Briefly, this disclosure concerns the removal of fibroid tumors and the like from breasts and possibly from other portions of the human body. A form of the invention includes a surgical instrument for isolating and excising a tumor from the tissue of a human body. A cannula includes a cylindrical sidewall and at least one opening in said sidewall. An open ended cutter may be telescopically received in the cannula, the cutter including a circular cutting edge for extending beyond the distal end of the cannula for cutting the tissue of the human body and forming a core of tissue surrounding the tumor and a cavity outside the core of tissue for receiving the cannula as the cannula and cutter are inserted in the tissue. Tumor positioning tines may be formed in a circular array and movable telescopically with respect to said open ended cutter for penetration of the tissue surrounding the tumor before the cutter forms the core of tissue. A garrote may be provided to cut the core of tissue loose from the surrounding tissue.

In one embodiment of the invention, direction indicia are applied to the proximal end of the cannula for indication of the radial direction at which a tumor or narrow margin about a tumor of a patient extends outside the incision. For example, the direction indicia may include clock markings such as 3, 6, 9 and 12, about the rim at the proximal end to the cannula, compass markings such as 0, 90, 180, and 270, or other direction indicia.

Once the incision has been made, the cutter may be removed from the cannula and from about the core of tissue that has been formed by the cutter, leaving the cannula in place about the core of tissue.

Another feature of the surgical instrument may be the use of a detection probe such as an ultrasound instrument in concert with the other elements of the device. The device may be open-ended and sized and shaped for telescopically receiving the detection probe or some other detection device, so that the detection probe may be positioned in contact with the tissue of the patient where the tumor is located for reading the precise position of the tumor. This tends to accurately position the device in alignment with the tumor. Once the device is properly positioned, the detection device may be removed during the remainder of the surgical procedure, or may remain in place in the device to continuously check the location of the tumor as the incision is formed.

The cannula may be formed with an opening in its sidewall, with the opening extending between approximately 70° to 100° about the sidewall of the cannula. After the initial incision has been made with the surgical instrument and the tumor excised, the pathologist might discover that a clear negative margin was not formed at one side of the tumor. Upon receiving the pathologist's report, the surgeon may rotate the cannula about its longitudinal axis so as to have its sidewall opening register with the tissue where more tissue may be removed to form the clear margin, and the surgeon may excise more tissue to form the desired margin.

The surgical instrument may include a carrier for mounting the other elements to be used in the process of excision of the tumor. For example, the carrier may be tubular with a detection probe mounted interiorly of the carrier and the other components mounted exteriorly of the carrier, such as the cannula and cutter.

Another embodiment may be the method of excising tumors from the tissue of a human body that includes placing a detection device upon the exterior tissue of the human body at the site of the tumor to locate the position and shape of the tumor, and using the detection device as a guide for advancing a cutter into the tissue. The cutter may be mounted telescopically about the detection device for moving in alignment about the detection device and into the tissue to form an incision that surrounds the tumor.

The surgical instrument may include a plurality of positioning tines that move into the tissue to stabilize the surgical instrument and to surround the tumor and stabilize the cutting function of the cutter. The positioning tines may be formed in an array that surrounds the tumor before the cutter is advanced into the tissue of the body. The cutter forms a core of tissue of the body that includes the tumor and the tines. The surgical instrument may be used to sever the core of tissue containing the tumor from tissue of the body, and extracting the core of tissue and the tines containing the tumor from the body with the tines remaining in the core.

The method of excising tumors from the body may include advancing the cannula and the cutter in telescoped relationship into the tissue of the body about a tumor to a depth that surrounds a core of tissue that contains the tumor. The surgeon may withdraw the cutter from the cannula, excise the core formed by the cutter and leave the cannula in place within the cavity formed by the cutter. The surgeon may rotate the cannula while the cannula is still in the incision to view through a side opening of the cannula into the tissue facing the cannula and excise additional tissue in registration with the opening of the cannula.

The positioning tines may be inserted about the tumor before performing the step of cutting about the tumor so that the tines guide the cutting function. When the core containing the tumor is excised, the core may be carried with the tines from the cavity.

Other procedures and devices are set forth in more detail hereinafter and are described in more detail in the claims appended hereto.

BRIEF DESCRIPTION OF THE DRAWINGS

FIG. 9 is an expanded view of the handle and the carrier indexing collar.

FIG. 10 is a cross section of the carrier indexing collar.

DETAILED DESCRIPTION

Figure 1:
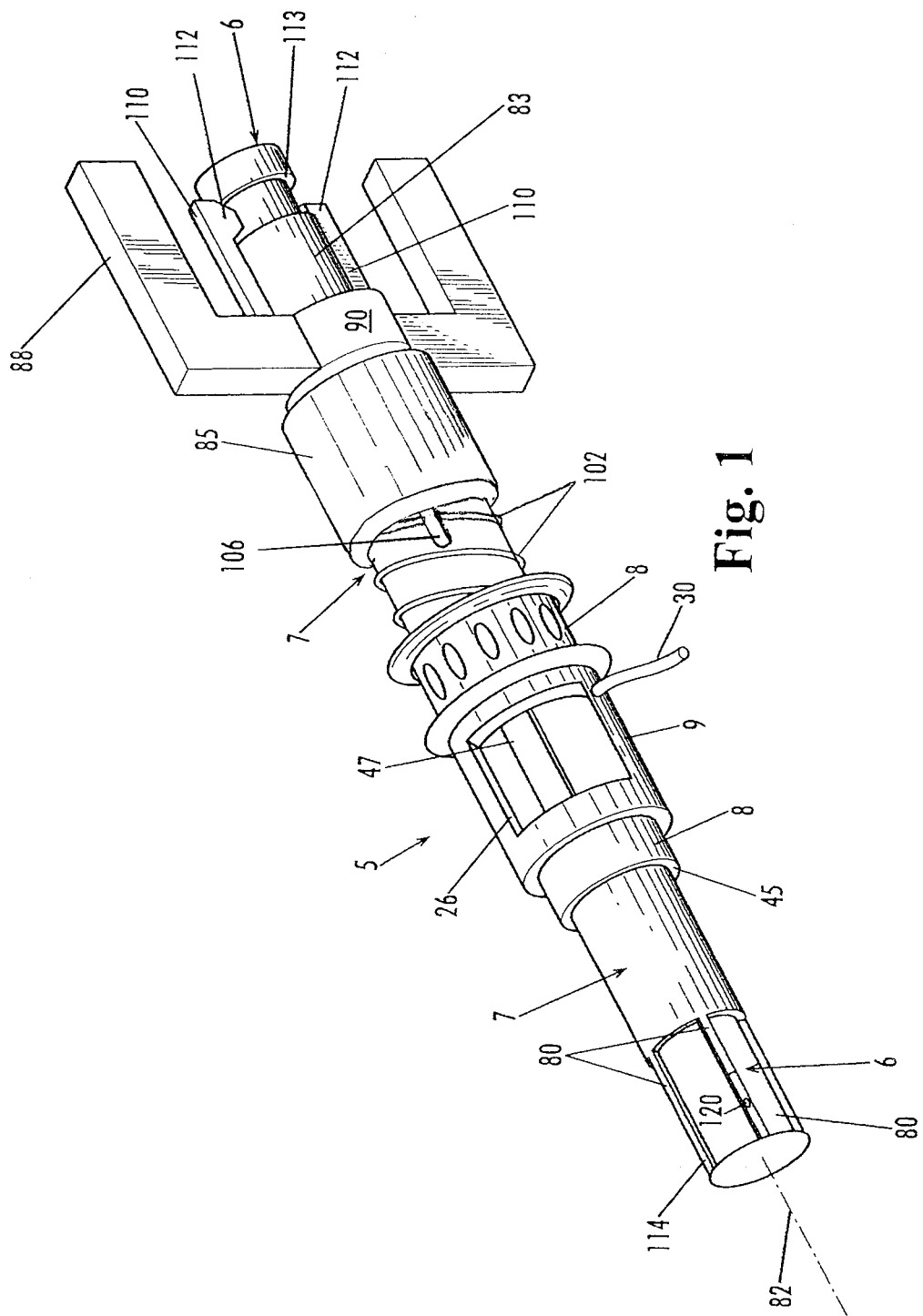
FIG. 1 is a perspective view of the surgical cutting instrument without the detection device, including both the cannula and cutter in telescoped relationship, showing the top and side surfaces thereof.

Referring now in more detail to FIG. 1, the assembled surgical instrument 5 includes an elongated detection probe such as an ultra sound instrument 6, a tubular carrier 7, a cutter 8 and a cannula 9. The tubular carrier 7, cutter 8 and cannula 9 may all be open ended and fit telescopically with respect to one another and telescopically about the detection probe 6, with the detection probe on the inside, the tubular carrier 7 next, the cutter 8 next, and the cannula 9 on the outside. The tubular carrier 7 is elongated and has an inner wall surface that telescopically fits about the detection probe so that the tubular carrier and the detection probe may be moved with respect to each other. Likewise, the cutter 8 and cannula 9 are shaped and dimensioned to be movable with respect to each other and movable about the tubular carrier.

Figure 2:
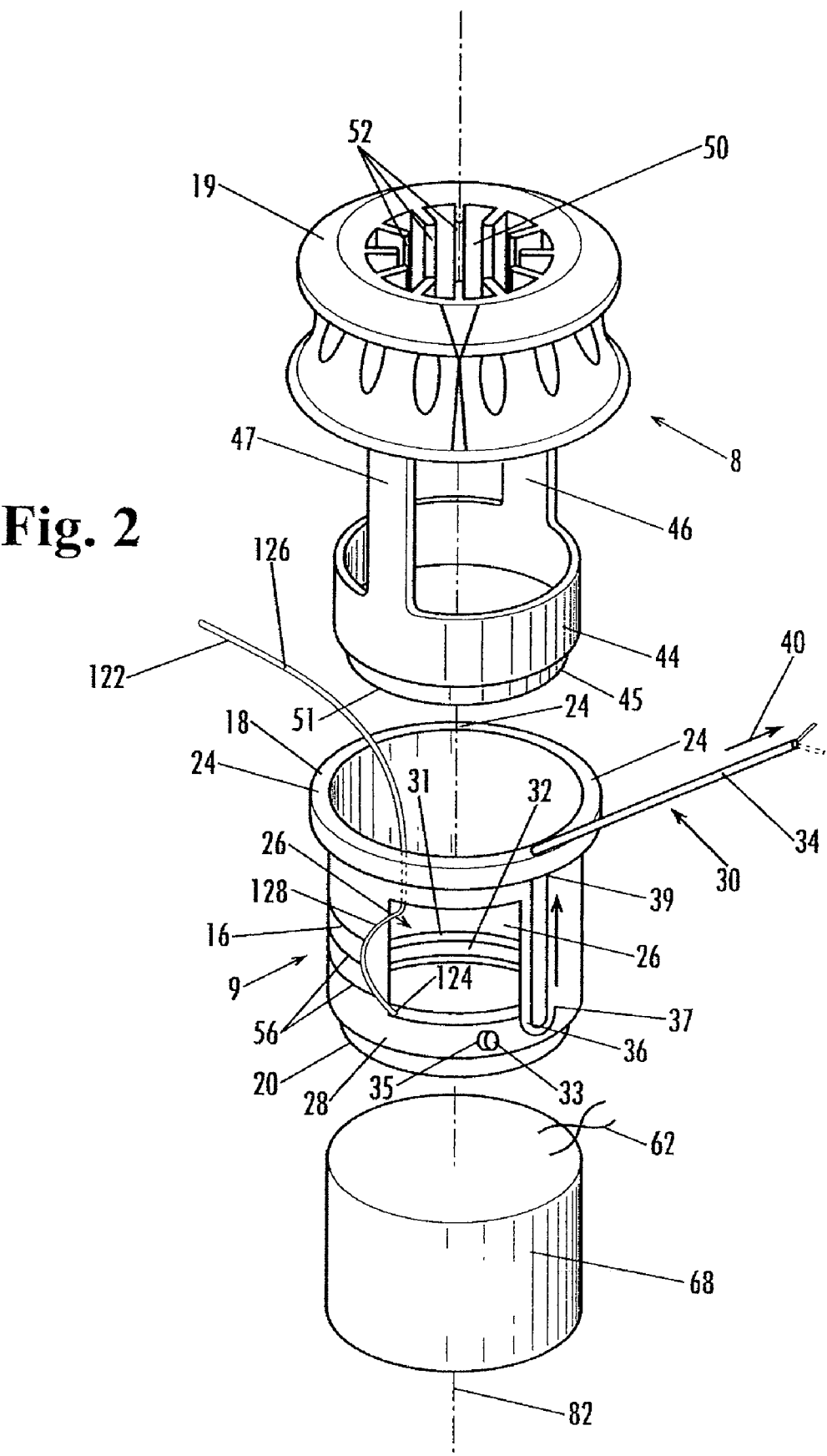
FIG. 2 is an expanded perspective view of the cylindrical cutter and cylindrical cannula of the surgical cutting instrument and a core of tissue cut from a patient.
Figure 3:
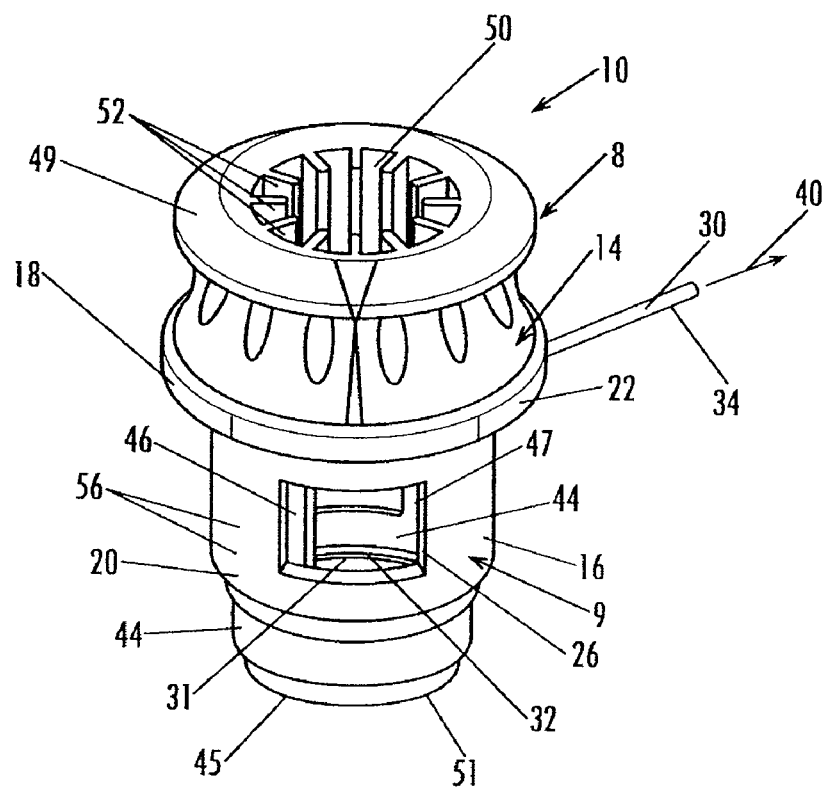
FIG. 3 is a perspective view of the assembled cutter and cannula.

As shown in FIGS. 2 and 3, the cannula 9 includes a cylindrical sidewall 16, a proximal end 18, and a distal end 20. The proximal end 18 includes a radially extending rim 22, and direction indicia 24 may be imposed on the rim. For example, the direction indicia 24 could include clock numbers such as 12, 3, 6 and 9; or compass numbers such as 0, 90, 180, and 270. Other direction indicia may be employed if desired, and the direction indicia may be placed on other parts of the cannula.

The cannula includes at least one side opening such as sidewall opening 26 that is formed in the cylindrical sidewall 16. The sidewall opening 26 may be generally rectangular and may occupy approximately 90° of the circular surface of the cylindrical sidewall 16. The height of the sidewall opening 26 may be 3 centimeters. The overall height of the cannula may be 5 centimeters. Other dimensions may be used as desired. The sidewall opening 26 may be of other shapes, such as oval or circular, as desired. The 12 o'clock position of the cannula 9 is aligned with the central portion of the sidewall opening 26 of the cannula.

The external surface of the cannula at its distal end 20 is beveled inwardly so as to reduce the resistance applied against the tissue during the insertion of the surgical instrument into the tissue of the patient.

As shown in FIGS. 2 and 3, a garrote wire 30 may be carried by the cannula 9. The garrote wire 30 includes an internal loop 32 that is received in a complementary shaped groove 31 formed on the inside surface of the cannula cylindrical sidewall. The loop of the garrote wire is positioned between the facing surfaces of the cylindrical cutter and the cannula. The distal end 33 of the garrote wire may be attached to the cannula as by forming an enlarged portion of the garrote wire that extends through and frictionally engages the side port 35 of the cannula. The garrote tail 34 extends from inside the cannula through another port 37, then extends upwardly to the rim 22 through rim port 39, and from there outwardly so that it may be grasped by the surgeon or connected to another surgical implement. The presence of the cutter within the cannula prevents the loop of the garrote wire from closing. Typically, the garrote wire includes an electrically conductive wire with insulation about its tail and little or no insulation about its loop, and an electrical charge is applied to the wire, causing the loop to become hot for cutting through the tissue at the base of the core of tissue inside the cannula.

When the cutter 8 is withdrawn from the cannula 9, the tail 34 of the garrote wire 30 may be pulled in the direction as indicated by arrow 40 in FIGS. 2 and 3 so as to contract the garrote loop 32, causing the garrote loop to become reduced in diameter and to cut through the tissue that is present within the cannula.

As shown in FIG. 2, cutter 8 includes a cutter ring 44, a pair of opposed support legs 46 and 47 that extend away from the cutter ring, and an enlarged hand grip 49 attached to the distal ends of the opposed support legs 46 and 47. The distal circular edge 51 of the cutter ring 44 is beveled and forms a sharpened circular blade for cutting through the tissue of the patient. This arrangement allows the cutter 8 to be inserted telescopically into the cannula 9 with the larger diameter hand grip 49 moved into engagement with the rim 22 of the cannula 9. The surgeon may push the cutter 8 and cannula 9 along the length of carrier 7 into engagement with the tissue of the patient and rotate the hand grip of the cutter 8, causing the cutter ring 44 to rotate as it cuts through the tissue of the breast and to progressively enter the breast.

Figure 4:
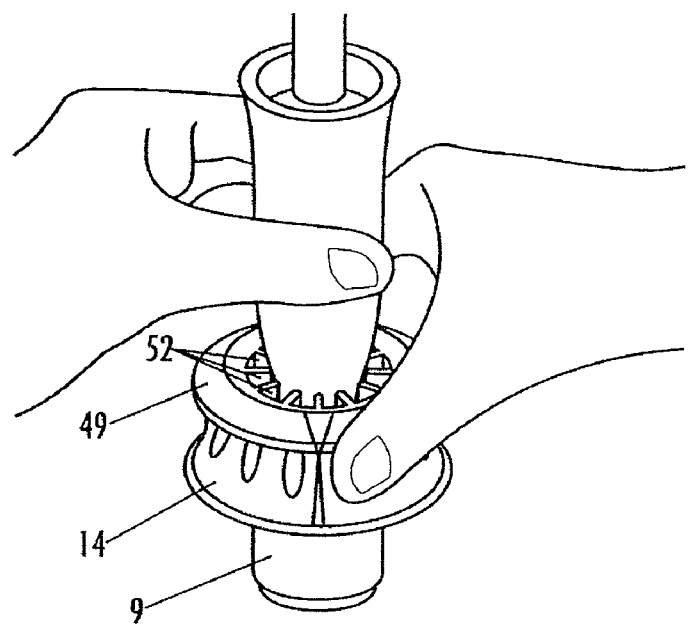
FIG. 4 is a perspective view of the cutter, showing how an ultrasound probe or other imaging device may be inserted through the open-ended surgical instrument for the purpose of locating the tumor and for positioning the surgical instrument in registration with the tumor.

Both the cannula 9 and the cutter 8 may be open-ended. The cutter 9 may be cylindrical and open-ended and include a longitudinal opening 50 that extends through the hand grip 49. An array of internal support fins 52 may extend radially inwardly of the opening 50 of the cylindrical cutter 8. As shown in FIG. 4, the internal fins 52 of the cylindrical cutter would be used to guide and support a smaller diameter detection device 54, such as an ultrasound detector as the detection device is passed through the open-ended surgical instrument. However the opening 50 of the cutter 8 and the external dimensions of the detection device may be formed with matching facing dimensions so the internal support fins 52 are not included in the design to form a snug fit between the detection device and the cutter.

The dimensions of the surgical instrument are such that the circular cutting edge 45 of the cutter 8 protrudes a predetermined distance beyond the distal end 20 of the cannula 9. This makes the cutting edge available for forming an incision in the tissue of the patient. The length of the legs 46 and 47 and the depth of the cutter ring 44 form the overhang of the hand grip 49 function to accurately position the cutting edge 45 at the predetermined distance beyond the distal end 20 of the cannula for forming the proper cut through the tissue of the patient. Depth marks 56 may be applied to the cannula to determine the depth made by the cutter into the flesh of the patient.

FIG. 2 illustrates the cutter 8 suspended above the cannula 9 and shows the core 60 of tissue below the cannula that is excised from the patient. The surgical instrument yields a substantially standard sized cylindrical core 60 that includes a smoother contour that may decrease the likelihood of false margins due to the pathologist's ink extending into crevasses in the specimen.

Given the more consistent cylindrical shape of the specimen, orientation of the specimen can be more precise, and marking the specimen in accordance with the directional markings on the cannula may be more accurately perceived by the pathologist. The surgical instrument more consistently excises a cylindrical core of tissue of a size that corresponds to the size and shape of the surgical instrument. Such a standardized specimen provides additional information to the pathologist regarding orientation of the specimen and allows for more specific assessment of any marginal involvement. In turn, the surgeon can more accurately excise additional tissue as may be needed to achieve clear margins at the first procedure, or when needed by reexcision.

Another benefit of the surgical instrument is that it yields a cavity in the tissue of the breast that is approximately cylindrical and of a standard size. This may improve cosmetic results and also the cavity may be used for partial breast irradiation using intra-cavity balloon brachytherapy as an alternative to external beam therapy, potentially reducing the treatment time of the therapy. Optimal use of the intra-cavity technique requires good conformation of the balloon to the lumpectomy cavity. The more standardized cavity dimensions may make this procedure more reliable.

Carrier 7 may be tubular, including an exterior wall surface 72 and an interior wall surface 74 with internal spiral threads 76 located near the distal end 77 of the carrier. Tine attachment 78 includes external threads 79 that are engageable with the internal spiral threads 76 for mounting the tine attachment to the distal end of the carrier. A plurality of elongated, parallel positioning tines 80 extend from the tine attachment 78. The positioning tines 80 are parallel to the longitudinal axis 82 of tubular carrier 7, cannula 8 and cutter 9 so that a circular array of parallel positioning tines is formed about the longitudinal axis.

Figure 8:
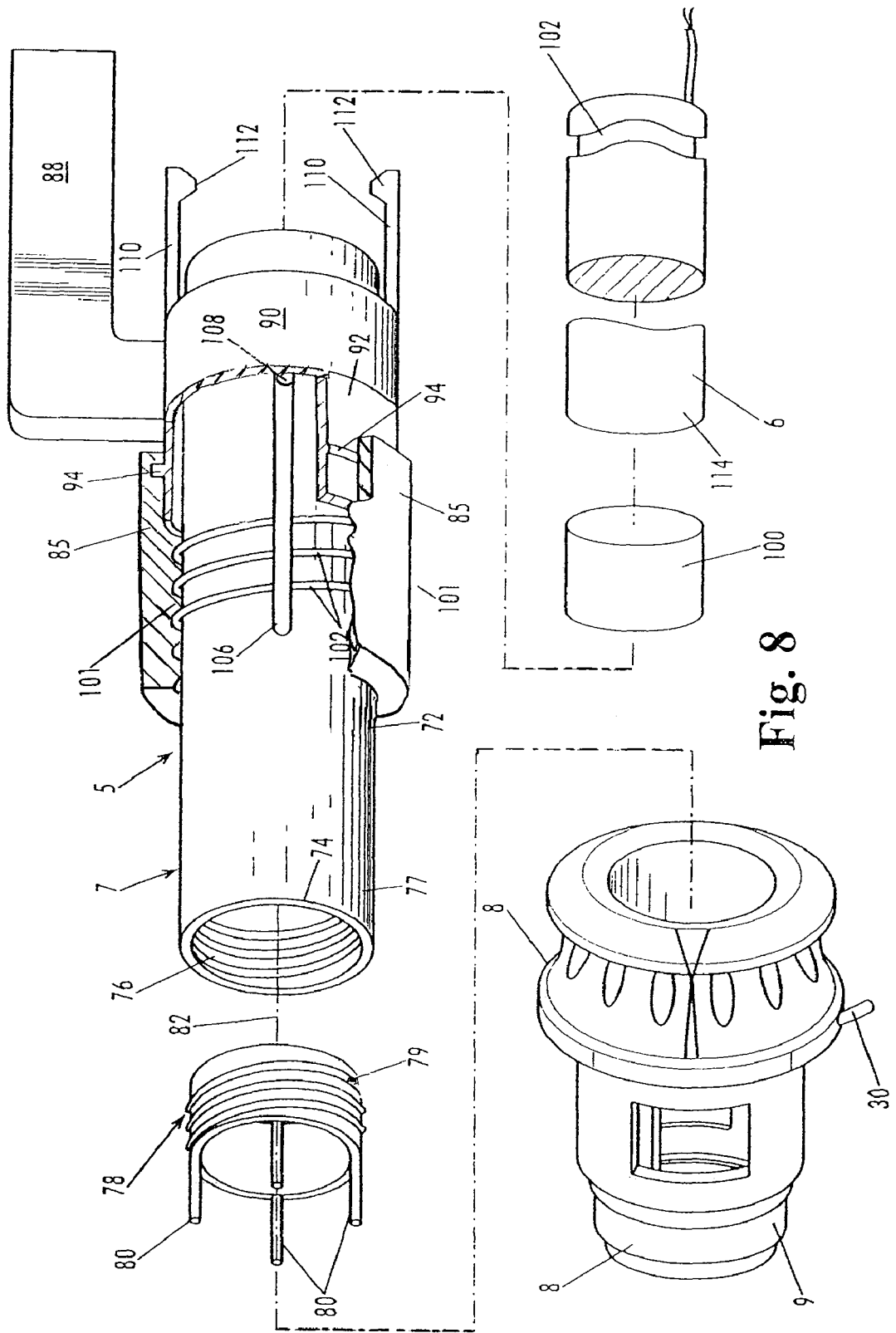
FIG. 8 is an expanded perspective view of the surgical instrument.

As shown in FIGS. 1, 8, and 9, the surgical instrument 5 also includes a handle 88 that is movably mounted to the carrier 7. Handle 88 includes a support ring 90 that surrounds proximal end 83 of the carrier 7 with the support ring being of larger internal diameter than the external diameter of the carrier so that the support ring 90 is movable telescopically along the length of the carrier. The support ring 90 includes a longitudinally protruding cylindrical flange 92 that includes an outwardly extending annular retaining bead 94.

As shown in FIGS. 8-10, interiorly threaded carrier indexing collar 85 is mounted to cylindrical flange 92 of support ring 90. The indexing collar 85 includes an inwardly facing annular recess 95 that extends about and into the annular retaining bead 94 of cylindrical flange 92. This mounts the indexing collar 85 to the cylindrical flange 92 in a manner that allows the indexing collar to rotate about the cylindrical flange 92, but avoids longitudinal movement of the indexing collar 85 with respect to the handle 88. Indexing collar 85 also includes internally facing spiral threads 101.

The intermediate portion of the tubular carrier 7 includes externally facing spiral threads 102 that register with the internal threads 101 of the indexing collar 85. A longitudinal guide groove 106 is formed in the exterior surface of the carrier 7, with the guide groove 106 interrupting the external threads 102 of the carrier. Handle 88 includes an internal guide protrusion 108 that registers with the longitudinal guide groove 106 so that the carrier and handle can move longitudinally with respect to each other but that other movements are avoided.

With this arrangement, when the indexing collar 85 is rotated about the carrier 7, the rotary movement of the internal threads 101 of the indexing collar in registration with the external threads 102 of the carrier 7 causes the carrier to advance along its longitudinal axis with respect to handle 88.

One or more positioning tongs 110 are supported by support ring 90 and extend rearwardly of the handle. Inwardly facing protrusions 112 of the positioning tongs 110 may be used to engage the detection probe 6 (FIG. 1) so as to hold the detection probe 6 in a predetermined location along the length of carrier 7. This allows the carrier 7, cutter 8 and cannula 9 to move with respect to the handle and the detection probe in response to the rotation of the carrier indexing collar 85.

Operation

When the surgical instrument 5 is to be used, the ultrasound instrument 6 is extended through the carrier 7 until the positioning tongs 110 of the carrier engage the groove 113 at the proximal end of the detection probe 6. The threaded carrier indexing collar 85 is rotated so that the indexing collar 85 retracts the carrier 7 until the longitudinal guide groove 106 is substantially retracted inside the confines of the threaded carrier indexing collar 85. The cutter 8 is telescopically mounted to cannula 9 and cannula 9 is telescopically mounted on the carrier 7, with the cutter and cannula moving from the distal end toward the proximal end of the carrier, until the cutting edge 45 of the cutter is moved back from the positioning tines 80. This places the surgical instrument in a condition where the distal end 114 of the detection probe 6 is positioned at the distal ends of the positioning tines 80, as shown in FIG. 1.

The surgeon will orient the surgical instrument so that it is substantially perpendicular to the surface of the breast or other anatomy part where the tumor is to be removed. The surgical instrument may be moved so as to properly align the surgical instrument with the tumor, with the positioning tines 80 oriented about the tumor. The surgeon may then rotate a threaded carrier indexing collar 85, which advances the carrier 7 and those surgical instruments mounted thereon toward the surface of the tissue of the patient. With this process, the positioning tines 80 tend to penetrate the tissue of the patient so that the tines progressively penetrate and surround the tumor. In the meantime, the detection probe 6 is allowed to retract progressively into the carrier 7 under the force applied by the patient's body to the distal end of the detection probe and in response to the gripping force of the positioning tongs 110 at the handle 88. This allows the detection probe to remain at the surface of the breast and the surgeon may continue to observe the read out of the detection probe as the positioning tines penetrate the patient's breast.

Once the surgeon is satisfied that the positioning tines 80 are properly positioned about the tumor, the surgeon may then advance the cutter 8 and cannula 9 along the longitudinal axis of the carrier 7 so that the cutting edge 45 of the cutter 8 forms a circular cut through the tissue of the patient. In the meantime, cannula 9 follows the cutter 8 so that the cannula and the cutter both enter the tissue of the patient.

Once the cutter 8 and cannula 9 have penetrated the patient, the cutter will have formed a core 60 (FIG. 2) of the tissue, with the tines 80 still penetrating the core. The cutter 8 can then be retracted out of the excision, leaving the tines 80 and cannula 9 in place in the patient's breast.

The garrote wire 30 may then be engaged by pulling the garrote tail 34 so that its garrote loop 32 tends to constrict about the inner end of the core 60, tending to separate the core from the other tissue of the patient. Since the cannula 9 is of greater longitudinal dimension than tines 80, the garrote wire will cut the tissue beyond the distal ends of the tines.

When in this condition, the surgeon may choose to leave the cannula 9 in place in the cavity formed by the surgical instrument and then withdraw the carrier 7, including the tines 80 from the patient. Typically, the tines will have sufficient frictional engagement with the core 60 excised from the patient so that the core 60 tends to be withdrawn with the surgical instrument out of the cannula 9 still impaled by the positioning tines 80. In the alternative, the surgeon can grasp the core 60 with tongs and extract it through the cannula.

At this stage, the surgeon may mark the core 60 with a thread, such as thread 62 of FIG. 2, indicating the orientation of the core with respect to the carrier 7. If desired, the surgeon may unscrew the tine attachment 78 from the tubular carrier 7 and transfer the tine attachment with the core 60 still impaled by the positioning tines 80 to the pathologist so as to make sure there is no mistake about the orientation of the core with respect to the patient's body.

In order to assure the pathologist will recognize the orientation of the core 60, one of the tines may be formed with a different shape or color and the surgeon will always apply the surgical instrument with the special tine oriented correctly to the patient's body to indicate direction of the core 60.

One of the tines 80 may include an opening 120 therein and the opening may be used to insert a marker therethrough such as a pin or a color or a thread or other marking device that orients the core 60 to show the "north" direction, for example, of the core taken from the patient.

Figure 5:
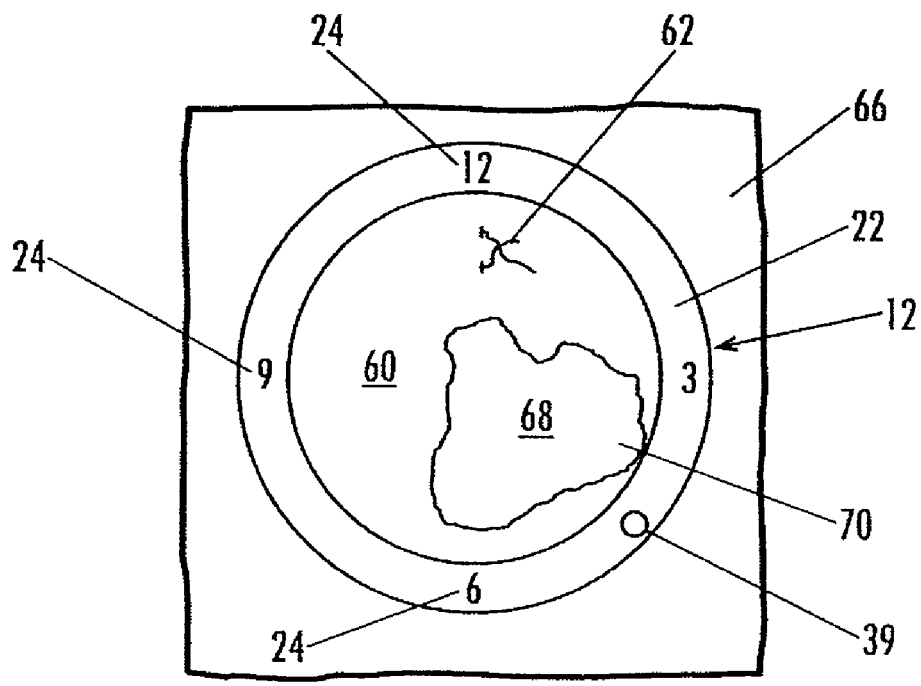
FIG. 5 is an end view of the cannula after it has been inserted in the tissue of the patient, showing the tumor surrounded by the cannula.
Figure 6:
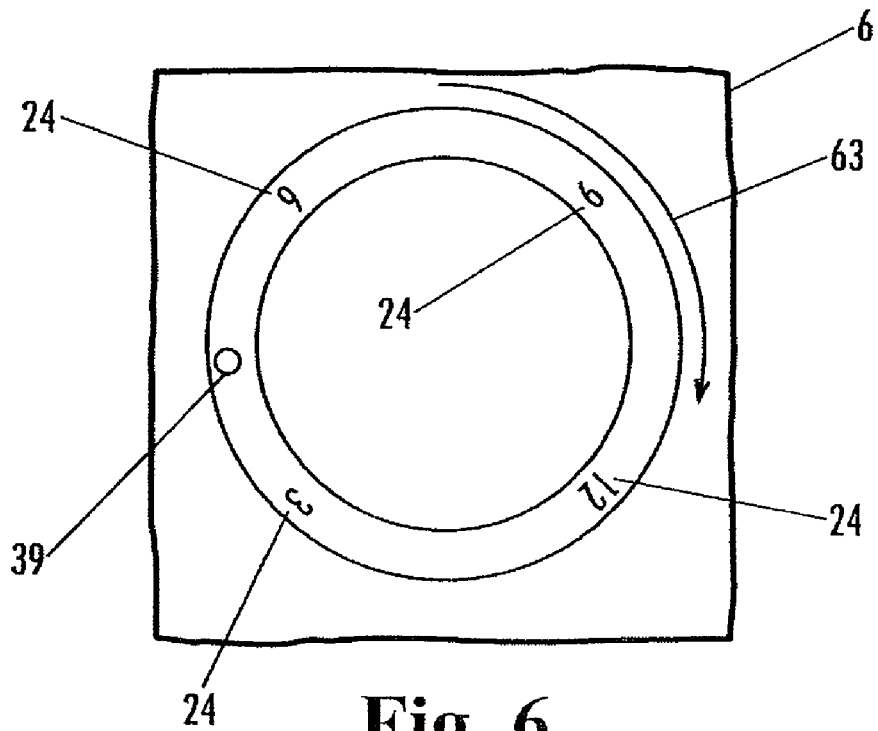
FIG. 6 is an end view of the cannula, similar to FIG. 5, showing how the cannula can be rotated so that its sidewall opening faces in the direction where more tissue is to be excised to form a clear margin about the tumor.

As shown in FIG. 2, the cannula 9 has its side wall opening 26 that allows the surgeon to visually inspect the interior surface of the incision made by the surgical instrument. Once the elements of the surgical instrument have been withdrawn from the excision, leaving only the cannula 9 in place, the cannula may be rotated as previously described so as to expose the interior surface of the excision, searching for any suspected tissue that should be excised. When the surgeon receives an indication from the pathologist that there is not enough clear margin between the tumor and the inside surface of the incision, as shown in FIG. 5, the surgeon can turn the cannula in its incision until the side wall opening faces the area adjacent the position of the tumor and can excise the tissue in that area. As shown in FIG. 2, one means of excising the additional tissue is a electrocautery wire 122 that has its inner end 124 anchored to the cannula adjacent the side wall opening 26, and with the intermediate portion of the wire 122 extending up through the side wall of the cannula, with a distal end 126 extending away from the cannula and within the grasp of the surgeon.

The electrocautery wire is of semi-rigid material so that when it is pushed along its length toward the cannula, and therefore compressed, it tends to form a bow 128 that is urged out into the tissue adjacent the side wall opening of the cannula. By rotating the cannula, the bowed portion 128 of the electrocautery wire 122 tends to cut exteriorly of the cannula, through the material in the path of movement of the bow 128. This excises the additional tissue adjacent the tumor 68 (FIG. 5).

Since the ultrasound instrument 6 that functions as a positioning probe is not expected to be sterilized, a sterilized shield 100 (FIG. 8) may be inserted over the distal end 114 of the detection probe. The shield 100 may be in the form of a flexible, sterilized material that may be shaped so as to form an internal surface that substantially corresponds to the shape of the distal end 114 of the detection probe. The shield 100 is mounted on the distal end of the detection probe 6.

Once the incision has been made to the proper depth as may be determined by markings on the positioning tines or on the cutter or carrier, the cannula will have been moved into proper position about the excision, and will hold the sides of the excision away from the space formed by the incision. The cannula typically will have its garrote moved beyond the tines 80 so that the garrote may be pulled and cut internally about the core 60 formed by the cutter. This is shown in FIG. 2.

While a garrote wire may be used as described, other means may be used to separate the core from the body.

The pathologist will inform the surgeon there is a negative margin about the tumor is not satisfactory and will inform the surgeon of the location of the inadequate margin. The pathologist will understand that the stitch 62 was formed at the 12 o'clock position of the core of tissue, and the pathologist can estimate the position of the inadequate margin. For example, FIG. 4 shows that the inadequate negative margin of tissue about the tumor is between the 3 o'clock and 4 o'clock positions when measured clockwise from the stitch 62.

Figure 7:
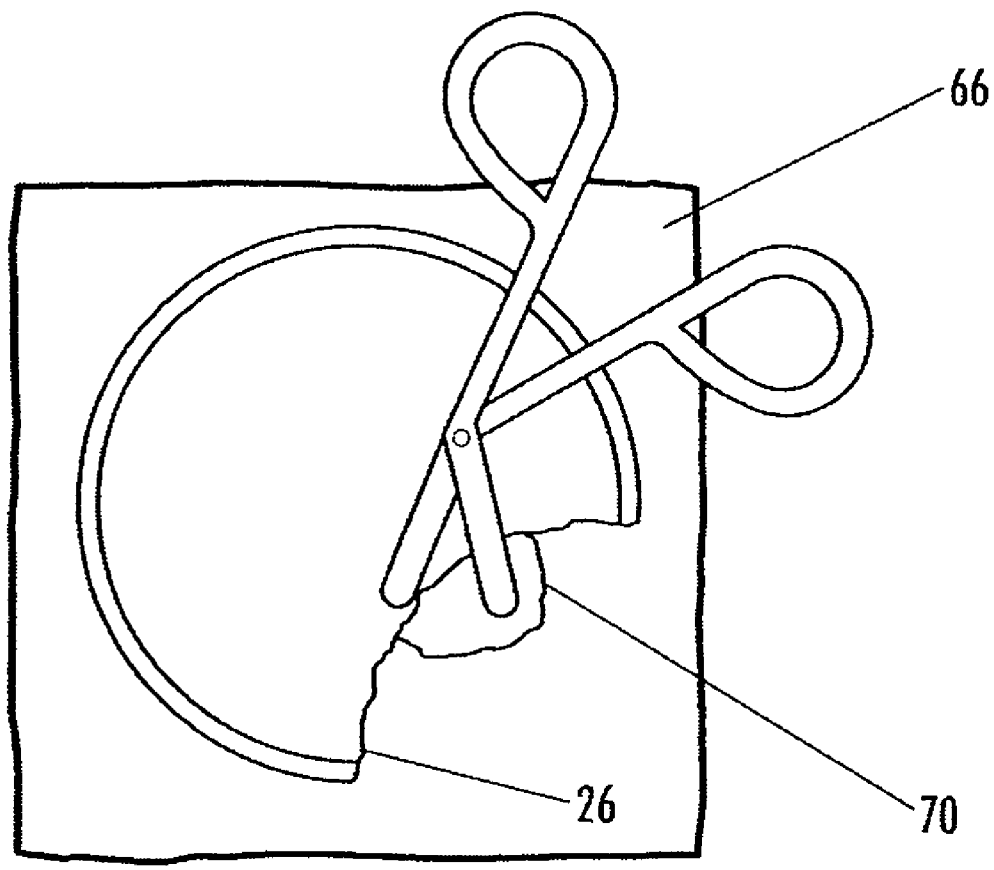
FIG. 7 is a plan view, similar to FIGS. 5 and 6, but showing how the surgeon uses a surgical instrument for grasping the adjacent tissue and pulling it into the confines of the cannula where it may be expediently excised by the surgeon.

With the above information, the surgeon will then be able to rotate the cannula in the breast of the patient as shown by arrow 63 until the 12 o'clock indicia faces between the 3 and 4 o'clock positions, as shown in FIG. 5. Since the 12 o'clock position on the rim of the cannula is aligned with the sidewall opening 26 of the cannula, the surgeon will then have the sidewall opening 26 in registration with the position of the inadequate negative margin 70 that was adjacent the tumor. The surgeon is then able to pull the inadequate margin of tissue through the sidewall opening 26 as shown in FIG. 7 with an appropriate surgical instrument and then surgically remove the portion of the tissue 70 at the inadequate margin.

Once this procedure has been accomplished, the cannula may be withdrawn from the incision and the tissue surrounding the cannula tends to collapse inwardly to close the wound. The surgeon completes the closing of the wound. The presence of the cannula in the incision tends to retard bleeding into the opening of the tissue.

An advantage provided by the invention is that one surgical procedure may be used for the expected incision about the tumor with clear negative margins about the tumor so that no reexcising of the portions of the tumor will be required. However, should there be an inadequate margin about the tumor, or if the tumor is discovered to extend out of the core, the reexcision as described above can be performed without having to perform additional surgery through the surface tissue of the patient. This tends to avoid the additional trauma that may be experienced by the patient for a follow-up surgical procedure.

The cannula and the cutter may be made of hard plastic, metal or other substances suitable for the intended use of the surgical instrument. If desired, parts of the device may be made of re-useable materials such as stainless steel.

The external dimensions of the cutter should match the internal dimensions of the cannula, with the circular cutting edge of the cutter protruding from the distal end of the cannula when the cutter is fully telescoped into the cannula. The cutter may be cylindrically shaped to surround the core of tissue to be removed from the breast of the patient.

While the invention has been disclosed for use in breast surgery, it may be used for other surgical purposes.

Although preferred embodiments of the invention have been disclosed in detail herein, it will be obvious to those skilled in the art that variations and modifications of the disclosed embodiments can be made without departing from the spirit and scope of the invention as set forth in the following claims.

The invention claimed is:

1. A surgical instrument for excising a tumor from the tissue of a human body, comprising:
    an open ended tubular carrier, said tubular carrier having a proximal end and a distal end and a longitudinal axis, said carrier sized and shaped to telescopically receive a detection probe through said proximal end and to be positioned at said distal end,
    a plurality of parallel positioning tines mounted to said distal end of said tubular carrier extending in a circular array about said longitudinal axis of said tubular carrier for penetrating the tissue of the human body about the tumor,
    an open ended tubular cannula telescopically mounted about the exterior of said tubular carrier and telescopically movable about said positioning tines,
    said cannula including a cylindrical sidewall and a distal end, and at least one opening in said cylindrical sidewall for exposing the tissue of the human body,
    an open ended tubular cutter telescopically movable about said tubular carrier and said positioning tines and received within said cylindrical sidewall of said cannula,
    said tubular cutter including a cutting edge for extending beyond said distal end of said cannula for forming a cylindrical incision in the tissue of the human body surrounding said positioning tines and forming an opening in the tissue for receiving said cannula as said cannula and said cutter are inserted in the tissue,
    such that when the surgical instrument has formed an incision in the tissue of the human body the tubular cutter may be telescopically withdrawn from within the cannula and the cannula may remain in the tissue of the human body and is rotatable in the incision to position the opening of the cannula toward tissue adjacent the cannula, and
    a garrote wire extending about the interior of said cannula and between said cannula and said cutter for severing the tumor from the tissue inside said the cannula from the human body.

2. The surgical instrument of claim 1 and further including a detection probe mounted in said carrier for detecting the tumor.

3. The surgical instrument of claim 2, wherein said detection probe comprises an ultrasound detection probe.

4. The surgical cutting instrument of claim 2, wherein said at least one opening in said cylindrical sidewall of said cannula extends between 70 degrees and 100 degrees about said cannula for passing a surgical instrument through said opening.

5. The surgical instrument of claim 1, and further including a sterile cover surrounding at least a portion of said detection probe.

6. The surgical instrument of claim 1, and wherein direction indicia are applied to said cannula in a circular array about said cannula for indication of the direction at which a tumor of the patient has spread toward the cut made by said cutter.

7. The surgical instrument of claim 1, wherein said garrote wire includes a loop that extends about the interior of said cannula between said distal end and said opening and a tail extending from said loop outside said cannula.

8. The surgical instrument of claim 1, wherein said cutter defines a longitudinal opening there through that includes an array of radial fins extending into the opening for slidably supporting the detection probe.

9. The surgical instrument of claim 1, wherein said tubular cutter includes a circular hand grasping rim, at least two support legs extending from said circular rim, and a circular cutting edge supported by said support legs, with openings formed between said support legs, said hand grasping rim and said cutting edge.

10. The surgical instrument of claim 1, and further including a handle surrounding said carrier, and a threaded carrier indexing collar movably supported by said handle and configured for distending said carrier from said handle in response to rotational movement of said carrier indexing collar with respect to said carrier.

11. The surgical instrument of claim 1, wherein said plurality of tumor positioning tines include indicia for indicating the depth of penetration of the tumor positioning tines into the tissue of the human body.

12. A surgical instrument for isolating and excising a tumor from the tissue of a human body configured for receiving an elongated detection probe for detecting the tumor, comprising:
 a tubular carrier including a cylindrical sidewall shaped for telescopically receiving therein the elongated detection probe as the detection probe determines the position of the tumor in the tissue, said cylindrical sidewall having a distal end for applying to the human body,
 a plurality of parallel elongated tumor positioning tines extending from the distal end of said tubular carrier and spaced parallel to one another for axially receiving the elongated detection probe as the detection probe detects the tumor and for penetrating the tissue of the human body and surrounding the tumor of the human body detected by the detection probe,
 an open ended tubular cutter shaped for telescopically surrounding and moving along the outside of said tubular carrier and along the outside of said tumor positioning tines for moving axially about said tumor positioning tines when the tumor positioning tines penetrate the tissue and forming an incision in the tissue about the tumor positioning tines, and
 a handle surrounding said carrier, and a threaded carrier indexing collar movably supported by said handle and configured for distending said carrier from said handle in response to rotational movement of said carrier indexing collar with respect to said carrier.

13. The surgical instrument of claim 12, wherein said tumor positioning tines are releaseably mounted to said carrier.

14. The surgical instrument of claim 12, and further including a cannula telescopically mounted about said cutter.

15. The surgical instrument of claim 14, and said cannula including a sidewall, and at least one opening in said sidewall sized and shaped to receive a surgical cutting instrument for excising tissue from about the cannula.

16. A surgical instrument for isolating and excising a tumor from the tissue of a human body, comprising:
 a tubular carrier,
 a plurality of positioning tines extending from said tubular carrier for penetrating the tissue of the human body and stabilizing the position of the tubular carrier with respect to the human body,
 said positioning tines being shaped and sized to support an elongated detection probe in contact with the tissue of the human body for detecting the tumor and for progressively retracting the detection probe into said tubular carrier in response to the force applied by the human body to the detection probe,
 a cylindrical cutter telescopically surrounding and movable along the exterior of said tubular carrier and along the plurality of positioning tines for engaging and forming a circular incision about the tumor in the tissue of the human body,
 a tubular cannula surrounding said carrier and said cutter for moving with said cylindrical cutter into the incision, said cannula including a cylindrical sidewall and an opening in said cylindrical sidewall for gaining access to the tissue adjacent said opening in said cylindrical sidewall, and
 a garrote wire extending about the interior of said cannula and between said cannula and said cutter for severing the tumor from the tissue inside said the cannula from the human body.

17. A method of excising tumors from the tissue of a human body, comprising:
 utilizing the surgical instrument of claim 1,
 placing a plurality of the tines into the tissue of the body in an array that surrounds the tumor,
 advancing the cutter about the tines into the tissue of the body,
 as the cutter is advanced into the tissue of the body, cutting with the cutter the tissue of the body and forming a core of tissue of the body that includes the tumor and the tines,
 severing the core of tissue containing the tumor from tissue of the body, and
 excising the core of tissue and the tines containing the tumor from the body with the tines remaining in the core.

18. The method of claim 17, wherein the step of severing the core of tissue containing the tumor from the tissue of the body comprises tightening the garrote wire about the core.

19. The method of claim 17, and further including marking the core at a position on the core that corresponds to a mark on the cannula.

20. A surgical instrument for isolating and excising a tumor from the tissue of a human body, comprising:
 a tubular carrier
 a probe for engaging the tissue of the human body for detecting the tumor in the tissue of the human body,
 a plurality of tines mounted to said tubular carrier and telescopically mounted about said probe for insertion in the tissue of the human body about the tumor,
 said probe progressively moveable along the tines in response to the movement of the tines into the tissue and the force applied by the tissue against the probe,
 a cutter sized and shaped to telescopically pass over said tines and to form a core of tissue containing the tumor and the tines and forming a cavity in the tissue surrounding the core of tissue, and
 a handle surrounding said carrier, and a threaded carrier indexing collar movably supported by said handle and configured for distending said carrier from said handle in response to rotational movement of said carrier indexing collar with respect to said carrier.

21. The surgical instrument of claim 20 and further including a cannula surrounding said cutter, said cannula including a side wall and at least one opening in said sidewall for movement in response to rotating the cannula about the cavity in the tissue to face the tissue outside the cannula.

22. The surgical instrument of claim 21, and further including direction indicia applied to said cannula for indicating a direction where a negative margin of tissue about the tumor in the core of tissue is not adequate.

23. The surgical instrument of claim 20, and further comprising a garrote wire extending about the interior of said cannula for separating the core of tissue containing the tumor from the body.

24. A surgical instrument for excising a tumor from the tissue of a human body, comprising:
 a tubular carrier defining a cylindrical sidewall having a longitudinal axis and a distal end, said tubular carrier sized and shaped to telescopically support therein a detection probe in engagement with the tissue of the human body,
 at least one positioning tine extending parallel to said longitudinal axis from said distal end of said tubular carrier for penetrating the tissue of the human body and for stabilizing said carrier in alignment with the tumor, a tubular cutter telescopically mounted about said carrier and movable beyond said distal end of said carrier and about the detection probe for forming an incision in the tissue about the positioning tines while the detection probe is in engagement with the tissue of the human body, and a tubular cannula telescopically mounted about said tubular cutter and movable with said tubular cutter, said cannula including a cylindrical sidewall defining a side opening for gaining access to the tissue beside the cannula, and a garrote wire extending about the interior of said cannula and between said cannula and said cutter for severing the tumor from the tissue inside said the cannula from the human body.

25. The surgical instrument of claim 24, wherein said cutter and cannula are cylindrically shaped and are sized for telescopic and rotary movement about said carrier.

26. The surgical instrument of claim 25, wherein said cutter is shaped to telescopically withdraw from said cannula.

27. The surgical instrument of claim 24, wherein said positioning tine comprises a plurality of positioning tines extending parallel to one another and extending from said carrier for engaging the tissue of the human body and stabilizing the carrier in a desired position of the human body during movements of the cutter about said positioning tines.

28. The surgical instrument of claim 27, wherein said positioning tines are oriented in a circular array that allows the detection probe to move through the circular array.

* * * * *